United States Patent [19]

Kleemann et al.

[11] 4,351,778

[45] Sep. 28, 1982

[54] PROCESS FOR THE RECOVERY OF MALONODINITRILE

[75] Inventors: Axel Kleemann, Hanau; Peter M. Schalke, Seligenstadt, both of Fed. Rep. of Germany

[73] Assignee: Degussa AG, Frankfurt, Fed. Rep. of Germany

[21] Appl. No.: 235,857

[22] Filed: Feb. 19, 1981

[30] Foreign Application Priority Data

Feb. 21, 1980 [DE] Fed. Rep. of Germany ....... 3006492

[51] Int. Cl.$^3$ ................... C07C 120/00; C07C 121/22
[52] U.S. Cl. .............................................. 260/465.8 R
[58] Field of Search ................................ 260/465.8 R

[56] References Cited

U.S. PATENT DOCUMENTS

| | | | |
|---|---|---|---|
| 2,553,406 | 5/1951 | Dixon | 260/465.8 R |
| 3,055,738 | 9/1962 | Krebaum | 260/465.8 X |
| 3,417,126 | 12/1968 | Taguchi et al. | 260/465.8 R |
| 3,549,684 | 12/1970 | Rosin | 260/465.8 R |
| 3,683,003 | 8/1972 | Aufdereggen et al. | 260/465.8 R |
| 3,729,499 | 4/1973 | Lussling et al. | 260/465.8 R |
| 3,867,422 | 2/1975 | Heimberger et al. | 260/465.8 R |
| 3,936,486 | 2/1976 | Egger et al. | 260/465.8 R |
| 4,136,108 | 1/1979 | Lassling et al. | 260/465.8 R |

FOREIGN PATENT DOCUMENTS

| | | |
|---|---|---|
| 1768154 | 9/1970 | Fed. Rep. of Germany . |
| 1911174 | 9/1970 | Fed. Rep. of Germany . |
| 2449013 | 4/1975 | Fed. Rep. of Germany . |
| 41-16506 | 9/1967 | Japan . |
| 49-4207 | 1/1974 | Japan . |

*Primary Examiner*—Joseph Paul Brust
*Attorney, Agent, or Firm*—Cushman, Darby & Cushman

[57] ABSTRACT

Malononitrile is obtained for the first time from its reaction gas mixture obtained by reacting acetonitrile and cyanogen chloride by partial condensation in decreasing temperature steps, namely while avoiding contact with the simultaneously formed hydrogen chloride.

11 Claims, 1 Drawing Figure

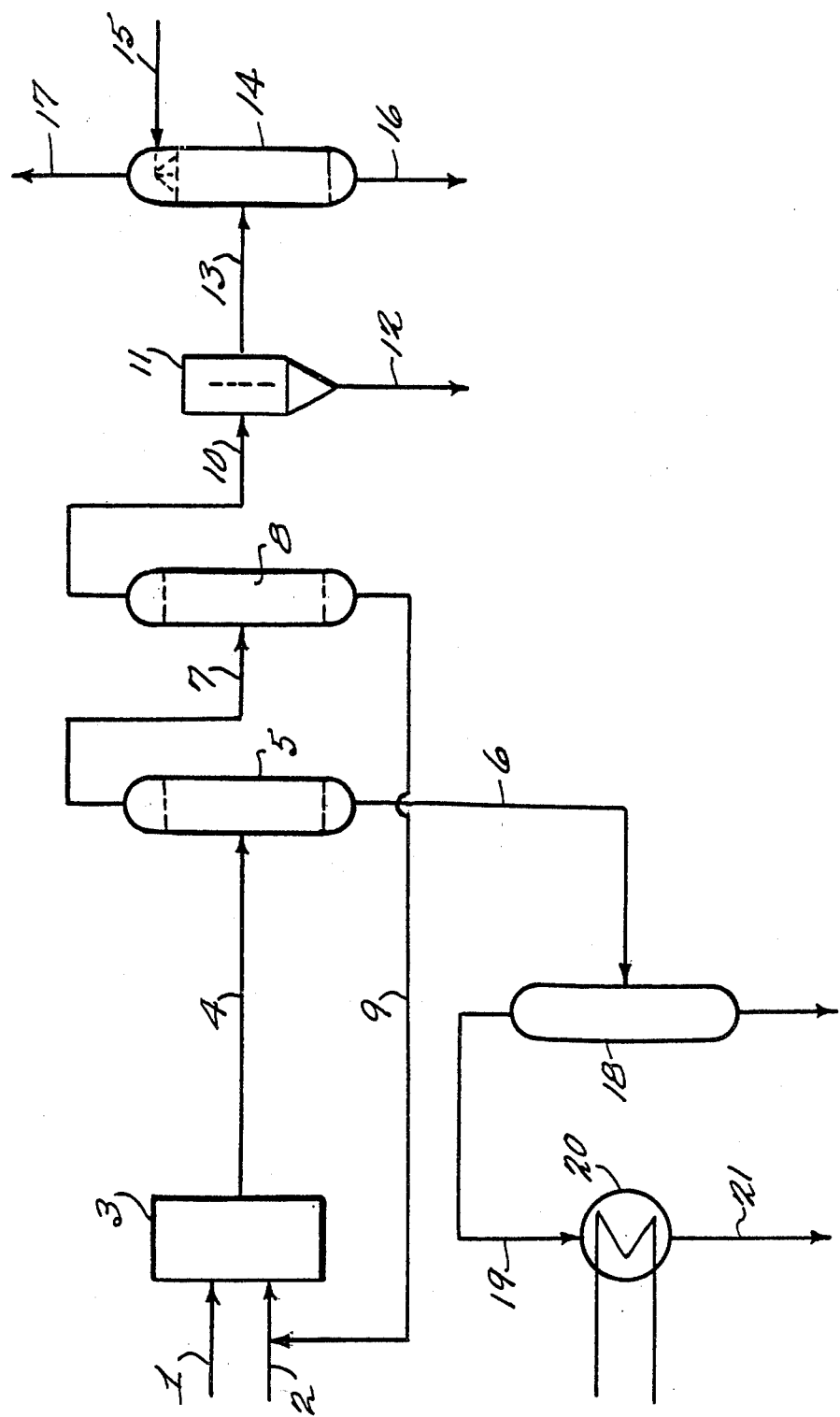

PROCESS FOR THE RECOVERY OF MALONODINITRILE

BACKGROUND OF THE INVENTION

Malonodinitrile (malononitrile) is known to be obtained by reaction of cyanogen chloride and acetonitrile at a temperature of 500° C. up to 1200° C., see e.g. Dixon U.S. Pat. No. 2,553,406, German OS No. 2449013, German Pat. No. 1768154, German Pat. No. 1911174 (and Lussling U.S. Pat. No. 3,729,499 related to both German Pat. Nos. 1768154 and 1911174); Japanese published application No. 41(1966)-16506; Taguchi U.S. Pat. No. 3,417,126.

The reaction is generally carried out without catalyst, see the above mentioned Japanese application No. 41(1966)-16506 and Taguchi U.S. Pat. No. 3,417,126. Also hydrogen cyanide, if present in larger than catalyst amounts, is employed to increase the selectivity, see Japanese Pat. No. 49-4207.

The great disadvantage in the production of malonodinitrile is in the very difficult isolation of the malonodinitrile from the reaction gas.

Generally the reaction gas is quenched as quickly as possible and thereupon the malonodinitrile recovered by fractional distillation, see e.g. Krebaum U.S. Pat. No. 3,055,738. The quenching is also assisted by use of a helping liquid such as acetonitrile itself, which can be either water free or water containing, as well as also by water or the condensed malonodinitrile itself, see German Pat. No. 1768154 and related Lussling U.S. Pat. No. 3,729,499.

However, the malonodinitrile can only be recovered from these quench solutions with losses.

The cause of these losses is based on the low stability of the malonodinitrile which can be decomposed explosively under the influence of strong acids or alkalis as well as with long heating above 100° C.

If there is employed water or water containing cooling agent then the aqueous hydrochloric acid solution formed thereby strongly saponifies the malonodinitrile formed. For this reason the reaction mixture during the cooling is simultaneously neutralized. The salt containing waste water formed in the process thereby, which contains besides highly toxic materials such as acetonitrile dissolved in water, unreacted cyanogen chloride, etc., is difficult to remove.

Also substituted malonodinitriles, such as, e.g. o-chlorobenzalmalonodinitrile are produced with a cooling liquid, in this case with o-chlorobenzaldehyde, into which the reaction gas of the reaction of acetonitrile and cyanogen chloride is led, see Rosin U.S. Pat. No. 3,549,684. Yield and purity of the product, however, are not stated.

Since the cooling medium for better distribution in the reaction gas and therewith to the quicker cooling is injected into the reaction gas there is the danger that in use of the condensed product solution itself there is the danger of the clogging of the nozzles by solid impurities present in the condensed product, such as, e.g. neutralization products.

Although the experts have known of the need of a better yield and an easier isolation they have always proceeded from the thoughts of a condensation of the entire gas mixture, possibly through use of a cooling liquid. This principle is also once more manifest in recent times in German Pat. No. 2449013, in which it is true that the cooling temperature is raised to at least 40° C. The condensed product solution itself serves as cooling agent. Through this, the formation of resin by saponification of the malonodinitrile because of the hydrochloric acid present should be avoided. If both the yields and the operating times of the quench part and of the after connected distillation part are to be improved then the resin formation as such is not eliminated.

In all of these processes particularly disadvantageous is the fact that the thermally sensitive malonodinitrile because of its higher boiling point can only be recovered after the distillation of the twofold to fivefold excess acetonitrile. Therewith it is heated for a long time at elevated temperature, through which decomposition products can form because of the thermal load and the yield lowered.

The object of the present invention therefore is the development of an industrially simple process that leads to the increase in yield of malonodinitrile (malononitrile) from the reaction gas.

SUMMARY OF THE INVENTION

It has now been found that malonodinitrile which was produced by reaction of cyanogen chloride, in a given case prepared from hydrogen cyanide, with acetonitrile can be recovered with an improved method of isolation and in higher yields from the reaction gas if the reaction gas resulting from the reaction at 500°-1200° C. is condensed in several successive temperature steps in which the first temperature step is the highest and the last temperature step is the lowest and the condensate obtained in each case separately worked up.

The malonodinitrile can be recovered in very favorably manner from the reaction gas mixture if the reaction gas is fractionally condensed in successive steps in such manner that the reaction gas is introduced, in a given case in concurrent or countercurrent flow with an inert gas, e.g. carbon dioxide, argon, helium or nitrogen, into a first condensation step whose temperature drop is to not below 80° C. and not above 170° C., the condensed crude malonodinitrile drawn off as sump product, the non-condensed portion, which in the main consists of unreacted acetonitrile, cyanogen chloride, as well as of the hydrogen chloride and byproducts formed during the reaction, is supplied to a second condensation step whose temperature drop is to between 20° C. and 82° C., preferably to between 25° and 82° C., the second condensate of residual acetonitrile and residual cyanogen chloride obtained thereby drawn off and in a given case the waste gas of hydrogen chloride, residual organic impurities, as well as in a given case inert gas, obtained hereby introduced into a third condensation step in which the hydrogen chloride and in a given case, inert gas, separated at a temperature of +50° C. to −100° C., preferably at −10° C. to −70° C., from small residues of organic impurities whereupon the crude malonodinitrile obtained in the first condensation step is distilled in known manner and in a given case in known manner purified by a recrystallization from a lower aliphatic alcohol, e.g. methanol, ethanol, isopropanol or propanol, the condensate obtained in the second condensation step preferably returned into the reaction step for the production of malonodinitrile and in a given case the hydrogen chloride from the gas leaving the third condensation step recovered by washing with water.

Acetonitrile and cyanogen chloride, as in the known process, are employed in the form of gases, likewise in the known molar ratios, e.g. 1:1 to 1:6. If inert gases are used during the fractionation there are especially used as these nitrogen and carbon dioxide.

There are used for the first and second condensation steps known fractionating columns which contain various kinds of plates or packings, preferably Sambay or falling film evaporators. Preferably the reaction mixture is led precooled into the first step. For the establishment of the desired temperature, e.g. a thermostatic fluid is used in the double jacket of the column or falling film evaporator which should not go below 80° C. as the lowest temperature in the first condensation step and should not exceed 170° C.

Corresponding temperatures are valid for the second and third condensation steps, i.e. in the second step the temperature of the liquid should not go below 20° C. or above 82° C., in the third step it should not go below −100° C. or above +5° C.

As thermostatic fluid in the first condensation step there can even be used steam for hot temperatures above 100° C. Generally, for this temperature range there are employed the known oils for this purpose.

The optimum temperature for the operation of the fractionating columns in the individual condensation steps are established with the help of analytical measurements in a preliminary test, since as is known they depend on customary column parameters such as height, diameter, type of packing or plates (if present), amounts fed in and flow velocities of the condensing gases.

BRIEF DESCRIPTION OF THE DRAWINGS

The single FIGURE of the drawing is a schematic diagram illustrating the direct fractionation of the reaction gases.

DETAILED DESCRIPTION

Referring more specifically to the drawings there are supplied to the reactor 3 chloride via line 1 and acetonitrile via line 2 and the reactants are reacted in the reactor.

The malonodinitrile containing gas leaves the reactor 3 and enters the fractionating column 5 via the cooled line 4. The separation into crude malonodinitrile which is drawn off via line 6 and gaseous reaction partner takes place in the fractionating column. The gaseous reaction partner together with the likewise gaseous hydrogen chloride, unreacted cyanogen chloride and organic byproducts are drawn off at the head of the column 5 via line 7 and is led into the fractionating column 8.

Here the unreacted acetonitrile and cyanogen chloride are condensed as completely as possible and is either drawn off as such (not shown) or preferably via line 9 led back to line 2 and then into the reactor 3 for the production of malonodinitrile.

The residual gas leaving the column 8 consists essentially of hydrogen chloride and in a given case inert gas, as well as lower boiling byproducts, such as e.g. adducts of cyanogen chloride and hydrogen chloride of unknown structure, as well as some acetonitrile.

As shown in the drawing this residual gas is led via line 10 into the separator 11 and there is freed from the organic impurities which are drawn off as liquids via line 12 and, in case desired, can be separately worked up (the last is not shown).

The gaseous hydrogen chloride freed from impurities flows via line 13 into a washing column 14 into which water is supplied via line 15. The aqueous hydrochloric acid solution leaves the system via lines 16. Depending on the amount of water supplied, there can be recovered concentrated or less concentrated hydrochloric acid solutions. Also, it is possible to use other washing agents such as alkaline solutions, e.g. of dilute alkali liquors, e.g. sodium hydroxide or potassium hydroxide or carbonate solutions, e.g. sodium carbonate or potassium carbonate; however, they do not lead to utilizable products such as with the use of water.

The possible use of inert gas, which leaves the system via line 17, for working up the reaction gas is not shown.

The crude malonodinitrile leaving the fractionating column 5 via line 6 enters the fractionating column 18 from which the pure malonodinitrile in vapor form is drawn off via line 19 and is condensed in condenser 20. The product is drawn off via line 21.

The third condensation step 11, however, can be eliminated if a working up of the residual gas is not of interest, e.g. in the presence of a plant for its destruction.

There are used for the first and second condensation steps and 5 and 8 known fractionating columns which contain various plates or packings, preferably Sambay or falling film evaporators. They are operated under apparatus pressure, preferably normal pressure. The third condensation step 11 generally consists of a heat exchanger which is operated with cooling brine. This heat exchanger can be connected before or behind with an activated carbon filter for the better adsorption of the byproducts. In place of activated carbon there can also be used other adsorption agents.

The process permits the direct isolation of the malonodinitrile from the reaction gas with increase of the yield, furthermore, the direct isolation of the acetonitrile employed in excess, which then can be immediately recycled in a cyclic process, in a given case with the residues of cyanogen chloride therein which have not reacted in the reaction, as well as the recovery of hyrochloric acid solutions. If the hydrochloric acid solutions are used again then there is no waste water.

Unless other indicated all parts and percentages are by weight.

The process can comprise, consist of essentially of or consist of the steps set forth with the stated materials.

EXAMPLE 1

78.9 grams (1.28 moles) per hour of gaseous cyanogen chloride were fed via line 1 and 280.8 grams (6.84 moles) of gaseous acetonitrile as well as 1–2 liters of gaseous nitrogen were fed via line 2 into the heated reactor 3 of the above one meter and having a diameter of 55 mm and an average temperature of 800° C. The product containing gas from the reactor 3 enters the column 5 via the cooled line 4. The column 5 consists of a "Sambay Evaporator" with an internal surface area of 0.1 $m^2$ and a packed column of 20 cm long placed thereon. Hot oil flows through the double jacket of column 5. At the foot of the column there were fed in 2 to 3 liters of gaseous nitrogen. The temperature of the oil in the double jacket is so regulated that the malonodinitrile crude product condensing in the foot of this column and having a temperature of about 160° C. can be drawn off via line 16, while the waste gas at the top of the column having a temperature of about 120° C. is led via line 7 into the fractionating column 8. The column 8 has a length of 50 cm, a diameter of 2 cm and is filled with Raschig rings. At the foot of the column there is led in per hour about 203 liters of gaseous nitrogen. The outer cooling so regulated over the double jacket that there prevails at the foot of the column a sump temperature of 82° C. and at the head of the column a temperature of 20°–40° C. The acetonitrile condensed in column 8 with the residues of cyanogen chloride contained therein is drawn off via line 9, returned to line 2 and mixed with fresh acetonitrile for supplementing the consumed material led into the reactor 3.

The residual gas leaving the column 8 is led via line 10 into a separator 11 consisting of a cooling trap held at −30° C. and there is freed from excess acetonitrile as well as from organic impurities which leave the system via line 2.

The residual gas freed from the impurities goes via line 13 through an activated carbon filter (not shown) into a washing column 14 in which there takes place the washing of the residual gases with water. There are obtained in column 5 per hour 69.2 grams of crude product which consisted of up to 91.2 weight % malonodinitrile and 4.8 weight % fumarodinitrile-maleic acid dinitrile and contained 0.7 weight % succinodinitrile. Acetonitrile was not detectable.

The crude product leaving column 5 was distilled in the fractionating column 18. The malonodinitrile boiling at 98°–99° C./13 mm after the distillation had a purity of 95–96%.

There accumulated in the column 8 223.9 grams of solution per hour which consisted of 98.1 weight % acetonitrile and up to 1.2 weight % cyanogen chloride. This solution was immediately returned to the reactor.

There were condensed 13.2 grams of solution per hour in separator 11. This solution had an acetonitrile content of 56.2% and must be worked up separately.

The titration of the aqueous solution of the gas washer 14 with caustic soda solution against methyl orange as the indicator give a HCl content which corresponds 95.8% of the hydrochloric acid formed from the cyanogen chloride.

From these results there were calculated yields of 79.3% based on acetonitrile and 74.5% based on cyanogen chloride.

COMPARISON EXAMPLE

There were fed into the same reactor 3 at an average temperature of 800° C. via line 1 78.9 grams (1.28 moles) per hour of gaseous cyanogen chloride and via line 2 280.8 grams (6.84 moles) of gaseous acetonitrile as well as 1–2 liters of gaseous nitrogen per hour. The product gas was let from the reactor 3 into a fractionating column in which the condensation of the entire amount of gas is carried out at 40° C. The residual gas leaving this column is washed with 40° C. warm product solution in a packed column. The waste gas was led over a separator held at −30° C. consisting of a cooling trap, then led through an activated carbon filter in a washing column filled with water. Here the residual gas was washed free of HCl.

By condensation of the product gas, there were obtained per hour 301.2 grams of solution in the fractionating column and in the separator which was worked up by distillation.

From a one hour experiment, there were recovered 229.3 grams of acetonitrile at a boiling temperature of 82° C. and having a purity of 98.9%. Subsequently, there were recovered by vacuum distillation at 98°–99° C./13 Torr, 61.8 grams of malononitrile having a purity of 92%. The distilled product furthermore contained 6.3% of fumarodinitrile-maleic acid dinitrile and 1.6% of succinodinitrile. It calculated as a yield of 67.1% based on cyanogen chloride and 68.6% based on acetonitrile.

In the distillation there were driven out of the solution a not inconsiderable amount of hydrochloric acid as well as cyanogen chloride. The titration of the contents of the washing column with caustic soda solution against methyl orange as indicator gave an HCl content which only corresponds to 64.8% of the hydrochloric acid formed from the cyanogen chloride.

In the comparison example the method of operation was according to German Pat. No. 2449013.

It can be seen that according to the process of the invention there was obtained a higher yield and a higher purity of the isolated product. Thereby the reactor in the comparison example and in the example according to the process of the invention was operated in the same manner.

What is claimed is:

1. In a process for the recovery of malononitrile prepared by reacting cyanogen chloride with acetonitrile at 500°–1200° C. and working up the reaction gas mixture, the improvement comprising fractionally condensing the reaction gas mixture alone or together with an inert gas in several successive temperature steps in which the first temperature step has the highest temperature and the last temperature step has the lowest temperature, the temperature drop in the first condensation step is to a temperature not below 80° C. and not above 170° C. thereby condensing the malonodinitrile as a first condensate, drawing off the condensed crude malonodinitrile as sump product, supplying the non-condensed portion which consists chiefly of unreacted acetonitrile and cyanogen chloride as well as hydrogen chloride and low boiling byproducts to a second temperature step between 20° C. and 82° C., thereby condensing the residual acetonitrile and cyanogen chloride as a second condensate and drawing off the second condensate and separately working up the condensate obtained in each step.

2. The process of claim 1 comprising condensing in a third condensation step the waste gas from the second condensation step and containing hydrogen chloride and residual organic impurities with or without inert gas at a temperature of +5° C. to −100° C. and thereby removing residual organic impurities therefrom.

3. The process of claim 2 wherein the third condensation step is carried out at −10° to −70° C.

4. The process of claim 1 comprising distilling the crude malonodinitrile obtained in the first condensation step to purify it.

5. The process of claim 1 comprising returning the condensate from the second condensation step to the reactor for forming further malonodinitrile.

6. The process of claim 1 including the step of recovering the hydrogen chloride subsequent to the second condensation step as hydrochloric acid by washing the waste gases with water.

7. The process of claim 2 including the step of recovery the hydrogen chloride after the third condensation step as hydrochloric acid by washing the waste gases with water.

8. The process of claim 7 including the steps of distilling the crude nitrile obtained in the first condensation step to purify it and returning the condensate from the second condensation step to the reactor for forming further malonodinitrile.

9. The process of claim 8 including the step of further purifying the distilled malonodinitrile by recrystallizing it from a lower alkanol.

10. The process of claim 1 comprising directly returning the acetonitrile obtained in the second condensation step to the reactor for the production of malonodinitrile.

11. The process of claim 10 wherein the acetonitrile returned to the reactor includes at least a portion of the residual cyanogen chloride obtained in the second condensation step.

* * * * *